(12) United States Patent
Ziemba et al.

(10) Patent No.: US 6,368,307 B1
(45) Date of Patent: Apr. 9, 2002

(54) FRONT-LOADING POWER INJECTOR AND METHOD OF LOADING FLANGED SYRINGE THEREIN

(75) Inventors: Robert J. Ziemba; Mitchell Smith; Charles S. Neer, all of Cincinnati, OH (US)

(73) Assignee: Liebel-Flarsheim Company, Cincinnati, OH (US)

( * ) Notice: Subject to any disclaimer, the term of this patent is extended or adjusted under 35 U.S.C. 154(b) by 0 days.

(21) Appl. No.: 09/697,204

(22) Filed: Oct. 26, 2000

Related U.S. Application Data

(63) Continuation of application No. 08/979,003, filed on Nov. 26, 1997, now abandoned, which is a continuation-in-part of application No. 08/896,695, filed on Jul. 18, 1997, now abandoned.

(51) Int. Cl.[7] .............................................. A61M 5/315
(52) U.S. Cl. ........................ 604/218; 604/131; 604/152
(58) Field of Search ................................. 604/152, 187, 604/181, 131, 151, 110, 134, 140, 143, 218, 227, 228

(56) References Cited

U.S. PATENT DOCUMENTS

| 4,342,312 A | 8/1982 | Whitney et al. |
| 4,465,473 A | 8/1984 | Rueegg |
| 5,279,569 A | 1/1994 | Neer et al. |
| 5,300,031 A | 4/1994 | Neer et al. |
| 5,383,858 A | 1/1995 | Reilly et al. |
| 5,520,653 A | 5/1996 | Reilly et al. |
| 5,779,675 A | 7/1998 | Reilly et al. |
| 5,899,885 A | 5/1999 | Reilly et al. |

FOREIGN PATENT DOCUMENTS

| WO | WO 97 07841 A | 3/1997 |
| WO | WO 97 36635 A | 10/1997 |

Primary Examiner—Angela D. Sykes
Assistant Examiner—Jeremy Thissell
(74) Attorney, Agent, or Firm—Wood, Herron & Evans, L.L.P.

(57) ABSTRACT

A power injector and a removable replacement faceplate therefor are provided along with a method of front loading syringes, particularly prefilled syringes, which have outwardly extending structure such as flanges which have been typically breech loaded or side loaded into injectors or operated in a hand held fashion. The holder or faceplate of or for the injector is provided with a set of jaws spaced around a syringe receiving opening into which a syringe is loaded, rearward end first, with the jaws in a retracted position, until the flange or other outwardly extending structure on the syringe is rearward of the syringe is beyond a locking position of the jaws. The jaws are then actuated, either by operating an actuator on the faceplate or injector or by twisting the syringe in the opening, so that the jaws move radially inward and close in iris-like fashion about the syringe. The jaws preferably engage a narrow ring along a juncture of the flange or other structure and the body of the syringe and make sufficient contact around the circumference of the syringe, with sufficiently small spaces between the contacting surfaces to avoid damaging deformation of the syringe during use and to effectively hold the syringe against forward forces exerted by the ram of the injector.

33 Claims, 4 Drawing Sheets

FRONT-LOADING POWER INJECTOR AND METHOD OF LOADING FLANGED SYRINGE THEREIN

This application is a continuation of the commonly assigned and now abandoned U.S. patent application Ser. No. 08/979,003, filed Nov. 26, 1997 and entitled "Front Loading Power Injector and Method of Loading Flanged Syringe Therein"; which is a continuation-in-part of now abandoned U.S. patent application Ser. No. 08/896,695, filed Jul. 18, 1997 and entitled "Adapter and Syringe for Front-Loading Medical Fluid Injector"; and are both hereby expressly incorporated by reference herein.

FIELD OF THE INVENTION

This invention relates to power injectors, and particularly to injectors of the front loading type, and to the loading of syringes into power injectors, particularly syringes of the flanged or otherwise rear loadable type.

BACKGROUND OF THE INVENTION

Power injectors are devices used to inject fluids at programmed or otherwise controlled rates or pressures into patients. Important uses include computed tomography (CT) and angiography, where a radiopaque contrast medium is injected into a patient's vascular system to enhance diagnostic images. With power injectors, a motor-driven ram advances the plunger of a syringe under the control, for example, of a microprocessor to provide control of injection parameters such as flow rate, flow volume and timing. Such injectors are often loaded with sterile empty syringes that are filled by drawing fluid from a supply into the syringe through the syringe nozzle by using the ram to draw the syringe plunger backward. In other situations, the injectors are loaded with prefilled syringes in which the fluid has been packaged in the syringe by media manufacturers.

Syringes of both the empty and the prefilled types are available in more than one design or style. The type of design or style of the empty syringes that are used by a practitioner are typically the choice, in part, of the practitioner and, in part, of the those selecting the injection equipment being used. With prefilled syringes, however, the choices of the practitioner are limited to the designs and styles provided by the prefilled syringe manufacturer, which may be limited due to the need of the manufacturer to submit the syringe and contents to various governmental approval processes. The time and costs involved in such processes as well as the costs of providing alternative syringe containers for each injection fluid product place practical and financial restraints on of the prefilled syringe manufacturer who might be attempting to provide a variety of physical syringe configurations in its product line.

A variety of syringe designs have been developed and are in use for both prefilled and user-fillable syringes. Many such syringes are provided with a radially outwardly projecting flange at their rearward ends which serve to hold or support the syringe against axial motion when force is applied between the flange and plunger by the power ram of the injector. Many syringes with radial flanges on their rearward ends were first developed for use in breech loading or rear loading injectors in which the rear loadable syringe is positioned behind a holder of the injector and translated forwardly, nozzle first, through an opening in the holder, so that the flange or other outwardly extending structure at the syringe rear will seat forwardly against the back surface of the holder. Usually the holder is in the form of a faceplate or door on the injector housing and opens by moving away from the injector housing, either in hinged or turret fashion, for the loading or unloading of the syringe into or from the injector. One such rear loading injector is described and illustrated in U.S. Pat. No. 4,695,271, which is assigned to the assignee of the present application, and is hereby expressly incorporated by reference herein. Injectors of this rear loading type were for many years a standard of the health care industry.

More recently, the assignee of the present invention has provided a front loading injector that receives front loadable syringes. A front loading injector is one in which a front loadable syringe is positioned in front of an opening in an injector holder and loaded into the holder by translating the syringe rearwardly, back end first, into the holder. These front loading injectors have a number of advantages that make them highly preferred. One such advantage is the ability to load the injector manually with a simple one handed motion, by merely rearwardly translating the syringe into an opening in the front of the injector, without opening a loading door, and then twisting or otherwise manipulating the syringe to lock it in place. Such a front loading injector is described and illustrated in U.S. Pat. No. 5,279,569, which is assigned to the assignee of the present application, and is hereby expressly incorporated by reference herein.

Notwithstanding the desirability of using front loadable syringes and front loading power injectors, it is often necessary to utilize prefilled or other syringes, which may be available only in a breech or rear loadable type. To accommodate practitioners in such situations, breech loading capability has been provided for front loading injectors of the type disclosed in U.S. Pat. No. 5,279,569, referred to above, by interchanging the syringe holding head structure of the front loading injector with a breech loading syringe holder that will accept flanged rear loadable syringes. The use of interchangeable heads nonetheless has required the practitioner to resort to the rear loading techniques of the older systems which still have the disadvantages that provided the motivation for their replacement.

Accordingly, there remains a need to provide the advantages of a front loading injector and the capability of using syringes, particularly prefilled syringes, of the rear loadable type, particularly those having flanged or other outwardly extending structure on their rearward ends that function to align or lock the syringe on the injector.

SUMMARY OF THE INVENTION

A primary objective of the present invention is to provide a power injector having the capability of being front-loaded with syringes, and more particularly with rear loadable, side loadable, hand operable and other syringes, including prefilled syringes and syringes having locking and aligning structure such as an outwardly extending flange at the rearward end thereof. A more particular objective of the present invention is to provide a front loading injector capable of being front loaded with syringes having flanges at the rearward end thereof and to provide a method of front loading such syringes into a power injector.

A further objective of the present invention is to provide a power injector, such as a front loading injector, with a alternative structure, such as a substitute syringe holder or faceplate, that will adapt an injector to be front loaded with syringes of the rear loadable type, particularly syringes having flanges at their rearward ends.

According to the principles of the present invention, a syringe holder is provided with a syringe receiving opening or cavity therein that is of a size and shape that will receive the rearward end of a breech loadable syringe when the syringe is translated axially rearwardly into the opening. The opening is provided with syringe gripping structure that moves from the periphery of the opening against the body of the syringe, to lock, align and orient the syringe in the opening.

In accordance with the preferred embodiment of the invention, an iris-like syringe holding mechanism is provided, such as, for example, a gripping mechanism including a plurality of jaws is arranged around the opening in a outwardly retracted position on the holder and are linked together. The jaws preferably function in an iris-like fashion, to reduce the size of the opening to that of the syringe body, thereby gripping the body immediately forward of the rearward end of the syringe. Structure on the rearward end of the syringe, such as a radially outwardly extending flange, for example of a type typical of a breech loadable prefilled syringe, is gripped in a slot between the jaws and a stop at the back of the opening, so that the syringe is locked in the opening, is aligned with its axis on the centerline of the opening and is oriented generally perpendicularly to the injector housing wall and parallel to and aligned with the injector ram.

In the preferred embodiment of the invention, the holder is removable, replaceable or exchangeable with holders of other configurations that are provided for supporting syringes of differing shapes or types, or for receiving syringes of the front loadable or rear loadable types. In an alternative embodiment of the invention, the holder with a syringe holding mechanism having iris like holding elements is provided as part of an injector.

With the present invention, breech loadable syringes, particularly prefilled syringes having various configurations of flanges, tabs or other outwardly extending structure at their rearward ends, are capable of being front loaded into and removed from the power injectors, and thereby have all of the advantages of front loadability, including those of high speed syringe replacement, the ability to load or remove a syringe with one hand, and the ability to remove a syringe while injection tubing remains connected to the syringe tip, and other advantages discussed in the incorporated patents cited above. The syringe holder of the present invention is capable of holding syringes with such radially or other outwardly extending structure on their rearward ends as well as syringes of a variety of other configurations, including syringes that lock to the injector at their rearward ends or elsewhere at other locations on the syringe.

These and other objectives of the present invention will be readily apparent from the following detailed description of the drawings.

DETAILED DESCRIPTION OF THE PREFERRED EMBODIMENTS

Figure 1:
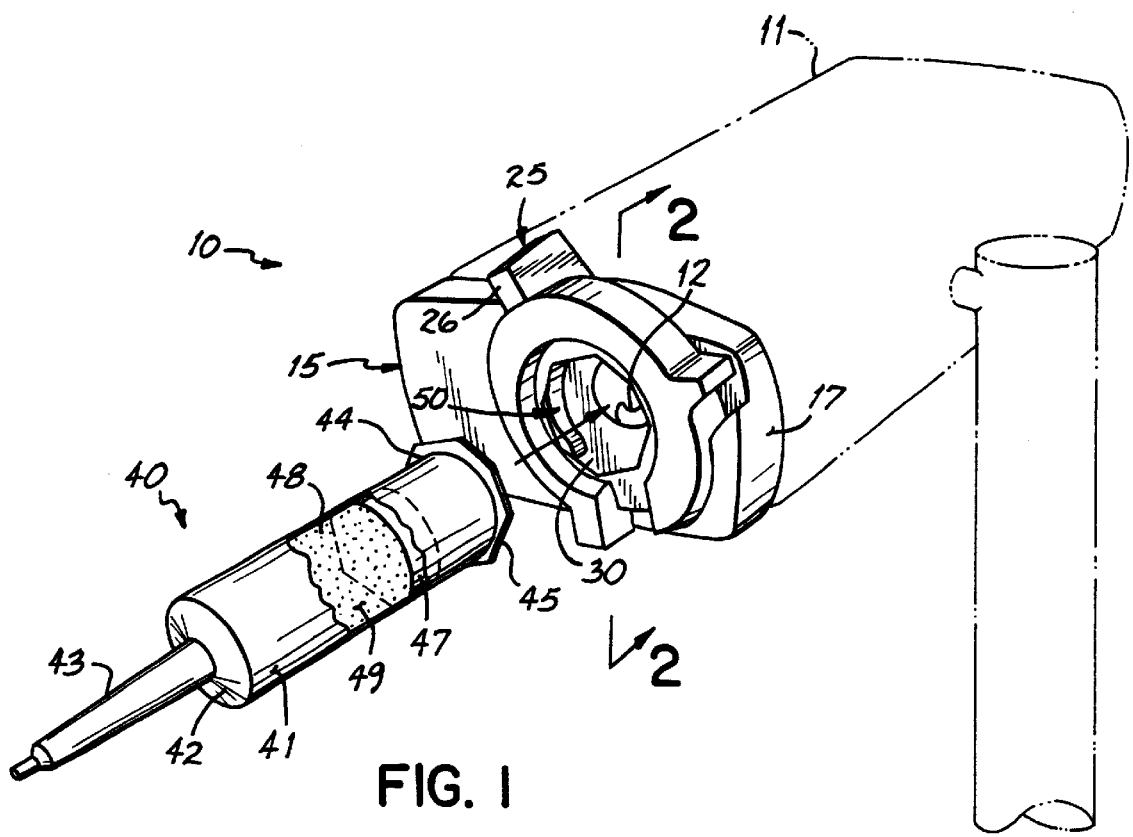
FIG. 1 is a perspective view of a front loading power injector according to principles of the present invention.

FIG. 1 illustrates a power injector 10 of a type, for example, that is used for angiographic and CT injection. One such injector is described and illustrated in U.S. Pat. No. 5,279,569, which is assigned to the assignee of the present invention, and is expressly incorporated herein by reference herein. The injector 10 includes an injector housing 11 that contains a power driven ram 12. The ram 12 is longitudinally extendable from the housing 11 in a direction normal to the front of the housing 11 by activation of a motor (not shown) contained within the housing 11. The forward end of the ram 12 is extendable from a retracted position in which its forward end is located inside the housing 11, as illustrated in FIG. 1, to an extended position in which its forward end has been advanced a considerable distance outside the front wall of the housing 11, as more fully explained in the incorporated U.S. Pat. No. 5,279,569. The injector described in that cited patent has a door assembly that constitutes a syringe mounting head of a front loading type for receiving a front loadable syringe with the syringe being loaded therein by translating it rearwardly, back end first, into the front of the mounting head.

The embodiment of the invention illustrated in FIG. 1 is, however, equipped with a faceplate in the form of a syringe mounting head 15 that is an alternative to, or a replacement for, or otherwise exchangeable with, the front loading head described in the patent which is configured to receive a syringe that is particularly designed for front loading, and which has a rearward end of the same outer diameter and cross-section as the syringe body. The mounting head 15 of the embodiment of FIG. 1 is rather configured to receive a syringe 40 of a type that has been designed for breech loading into an injector of the rear loading type, where the syringe 40 is translated, front end first, through an opening from the rearward side of a loading door, which must be opened for the purpose of loading or unloading a syringe 40.

The syringe 40 typically has a cylindrical syringe body 41 with a frusto conical front end 42 having a conical injection nozzle 43 at the front thereof. The syringe body 41 has a rearward end 44 provided with a radially outwardly extending flange 45. The flange 45 is typically of uniform thickness and integrally formed with the syringe body 41 at its extreme rearward end. The flange 45 may be a ring shaped annular flange with a circular outer edge, but usually is provided with at least one flat edge or notch to angularly align the syringe or to prevent the syringe from rotating about its longitudinal axis. The flange 45 of the syringe 40 has a polygonal outer edge that will angularly orient, or prevent rotation of, the syringe 40 when mounted in an injector. As illustrated in FIG. 1, the syringe 40 is provided with a flange 45 having an outer edge of octagonal shape. Within the body 41 of the syringe 40 is a plunger 47 formed of a hard polymeric material which forms a slidable but sealable contact with the inside of the syringe body 41 and defines along with the body 41 a sealed cavity 48 within the body 41 which contains injection fluid 49, preferably the syringe 40 when supplied from the manufacturer, that is, a prefilled syringe.

Figure 2:
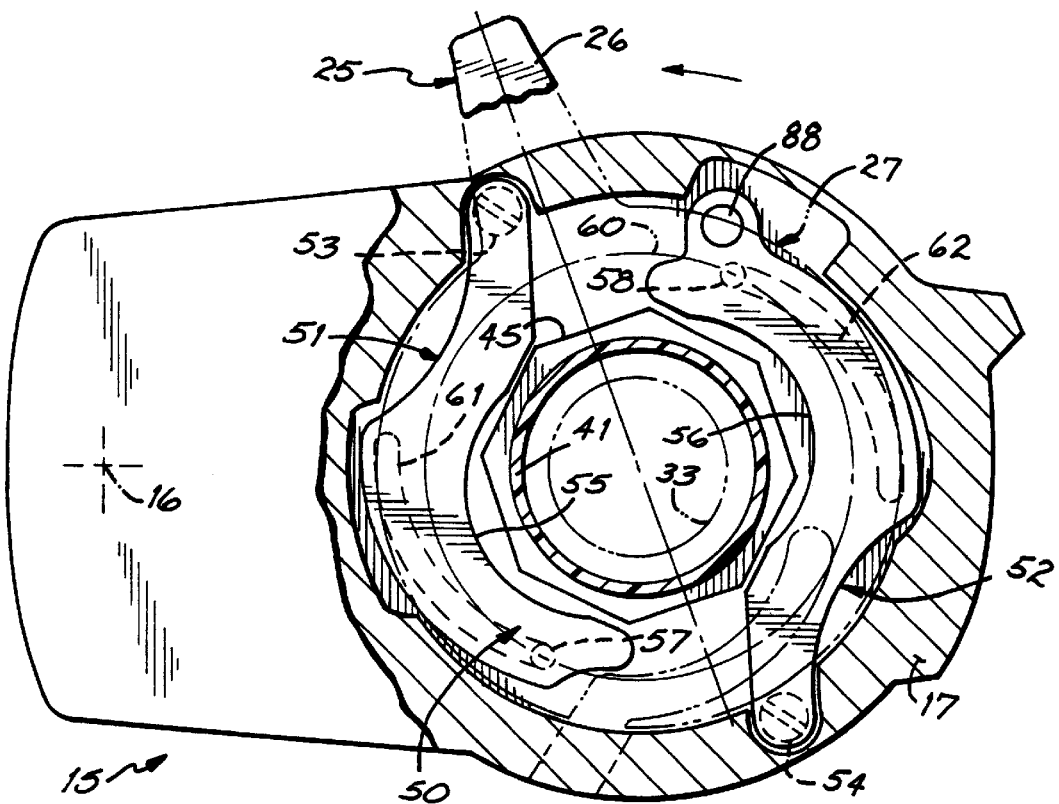
FIG. 2 is a partial cross-sectional view along line 3—3 of FIG. 1, showing the injector with its syringe gripping structure in a retracted position.
Figure 3:
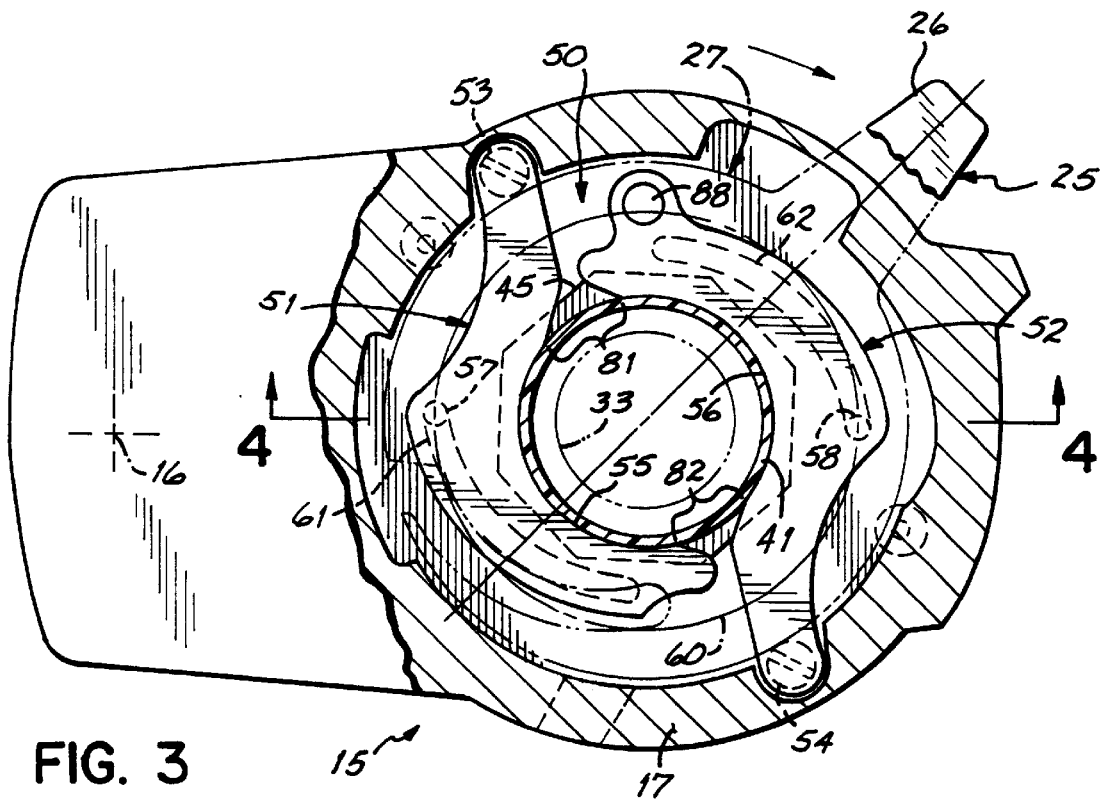
FIG. 3 is a view, similar to FIG. 2, with the gripping structure in a closed or locked position.

The head 15 preferably includes a casting 17 removably pivotally connected to the front of the housing 11 to a pivot shaft 16 and with a locking mechanism 25, which illustrated in part in FIGS. 1–3, and as is more particularly described in the incorporated U.S. Pat. No. 5,279,569. The mechanism 25 functions to lock and unlock of the head 15 to and from the housing 11, to couple the ram 12 to plunger 47 within the body 41 of the syringe 40, and to lock the syringe 40 to the injector 10. The mechanism 25 is provided with an operating lever 26, illustrated in an unlocked or loading position in FIGS. 1 and 2., which is the position which allows the head 15 to be opened, removed and replaced and which allows syringes 40 to be loaded and unloaded from the mounting head 15. The lever or handle 26 is connected to a disc 27 rotatably mounted to the casting 17. The handle 26 is moveable to a locked position, illustrated in FIG. 3, which is the position at which the head 15 is locked to the injector 10, the ram 12 is coupled to the syringe ram and the syringe 40 is locked to the injector 10.

Figure 4:
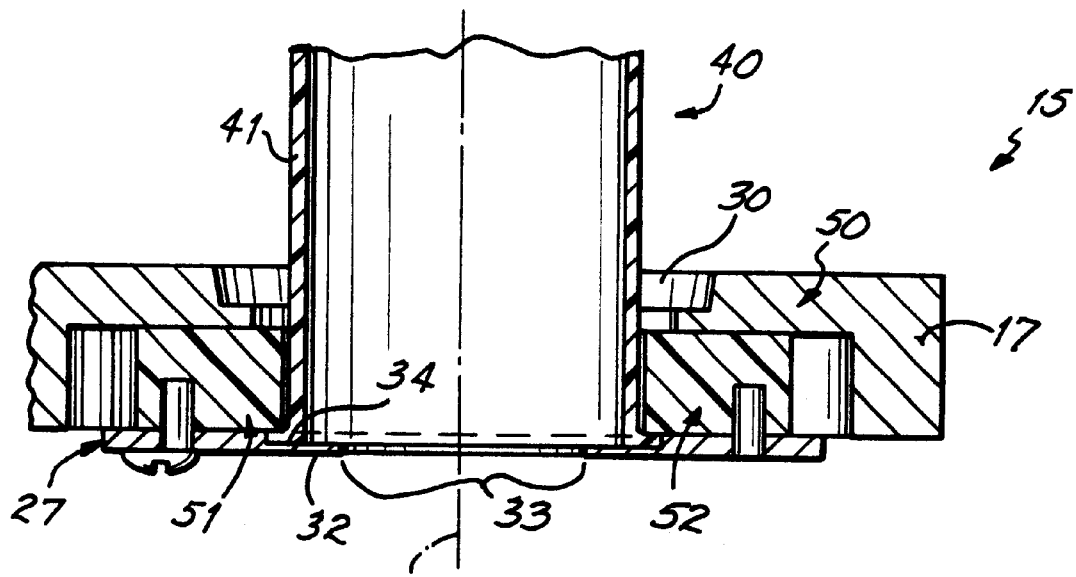
FIG. 4 is a cross-sectional view along line 4—4 of FIG. 3.

The casting 17 of the head 15 has an opening 30 therethrough, which is preferably of the same shape as the flange 45 of the syringe 40 and slightly larger in size to allow the flange 45 to be inserted into the opening 30. The opening 30 is preferably flared outwardly on the forward side thereof to guide the flange 45 of a syringe 40 into the opening 30 when the syringe 40 is being loaded. The opening 30 is centered on an axis 31 which is perpendicular to the front of the housing 11. The axis 31 is parallel to the path of the ram 12 and generally lies on the centerline of the ram 12 when the lever 26 is in its locked position. Behind the opening 30 is an annular stop 32 (FIG. 4), which lies in a plane that is oriented perpendicular to the axis 31. The stop 32 may be integrally formed of or otherwise fixed to the disc 27, which is centered to pivot on the axis 31. The stop 32 lies at the back of a recess 34 formed in the disc 27. The recess 34 has a depth approximately equal to the thickness of the flange 45. The recess 34 is preferably of the same shape as the flange 45 to hold the syringe 40 against rotation in the opening 30 once the syringe 40 is mounted in the opening 30. The stop 32 has an opening 33 therein to allow passage of the ram 12. When the flange 45 of a syringe 40 is inserted through the opening 30 and is seated against the stop 32, the axis of the syringe 40 coincides with the axis 31 of the opening 30, whereby the syringe 40 is perpendicular to the faceplate 15, and the syringe 40 is in its operating position on the injector 10.

According to one embodiment of the invention, the locking mechanism 25 includes a iris-like gripping mechanism 50 for holding the syringe 40 firmly in its operating position in the holder 15. The gripping mechanism 50 includes a plurality of gripping elements which preferably have gripping surfaces that encircle most of the circumference of the syringe body 31. In this embodiment, a pair of jaws 51,52, is provided, each jaw being pivotally connected to the housing 17 of the head 15 at respective pivot pins 53,54 which are fixed to the housing 17. The jaws 51,52 have inner concave gripping surfaces 55,56 having curvatures that correspond to the curvature of the outer surface of the body 41 of syringe 40. Preferably, the surfaces 55,56 of the jaws 51,52 each encompass an arc of between 90° and 180°, so that when the jaws 51,52 are closed (FIG. 3) the surfaces 55,56 substantially surround the body 41 of the syringe 40 and securely hold the syringe in the operating position. The jaws 51,52 are spaced forward of the stop 32 so that, when the syringe 40 is in its operating position, the syringe flange 45 is held flat against the stop 32 by the jaws 51,52.

The jaws 51,52 are simultaneously moved between retracted positions (FIG. 2) and locked positions (FIG. 3) by a camming action of the mechanism 25, which is provided by a pair of cam follower pins 57,58 mounted on the ring 27 to move with and be actuated by the handle 26. A magnet 88 is provided on the jaw 52 which can be detected by a sensor (not shown) in the injector housing 11 in order to determine that the mechanism 25 is in its locked condition which enables, through controls (not shown) in the housing, the operation of the ram 12. The pins 57,58 scribe an arc on a circle 60, centered on the axis 31, when the handle 26 is operated. The pins 57,58 move in arcuate slots 61,62 in the jaws 51,52, respectively, so that, when the handle 26 is operated, the pins 57,58 move the slots 61,62 generally radially and thereby cam the jaws 51,52 to pivot on their respective pins 53,54 between their retracted positions, in which the surfaces 55,56 are displaced radially outward of the flange 45 to provide clearance for the flange 45 when the flange 45 moves between the opening 30 and the backplate 32 during loading and unloading, and their locked positions in which the jaws 51,52 seat snugly against the outside of the body 41 of the syringe 40 immediately forward of the flange 45. When so actuated, the jaws 51,52 move generally radially inwardly or outwardly along a path that may be, but is not necessary normal to the outer surface 41 of the syringe 40.

Figure 5:
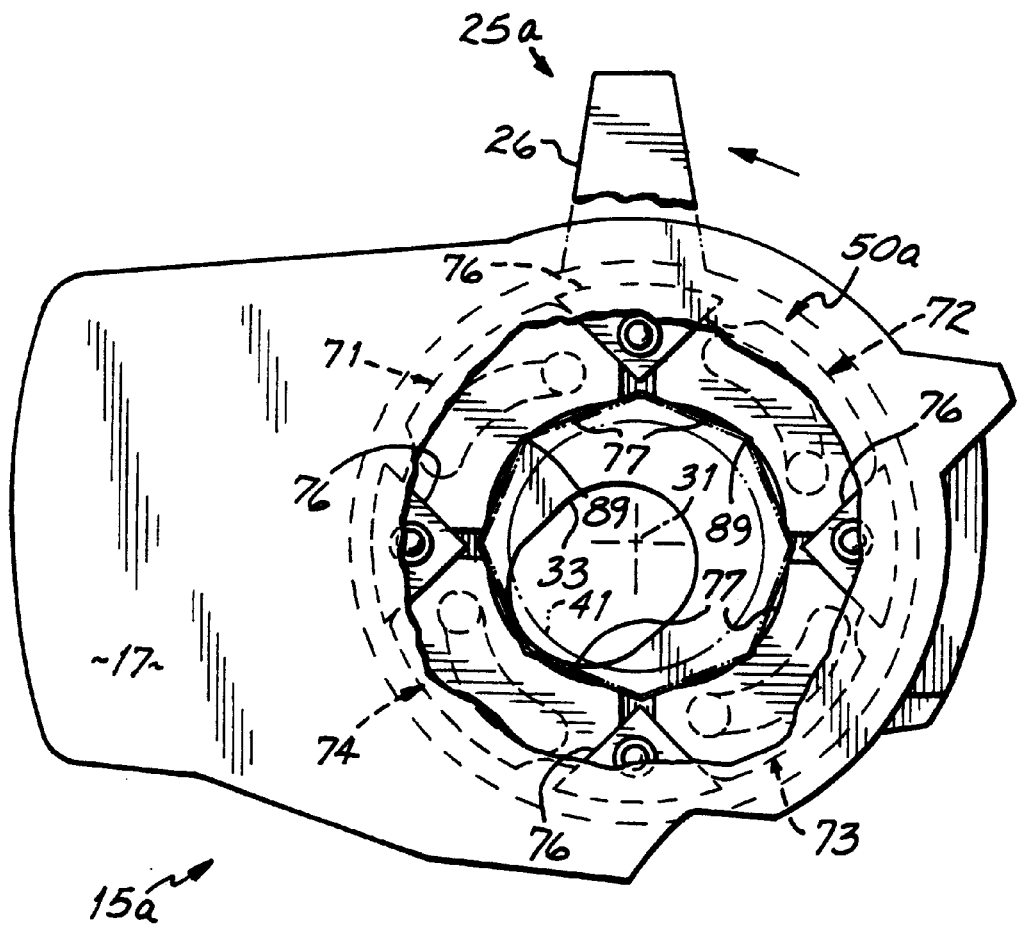
FIG. 5 is a front view of an alternative embodiment of the power injector of FIG. 1, showing the syringe gripping structure in a retracted position.
Figure 6:
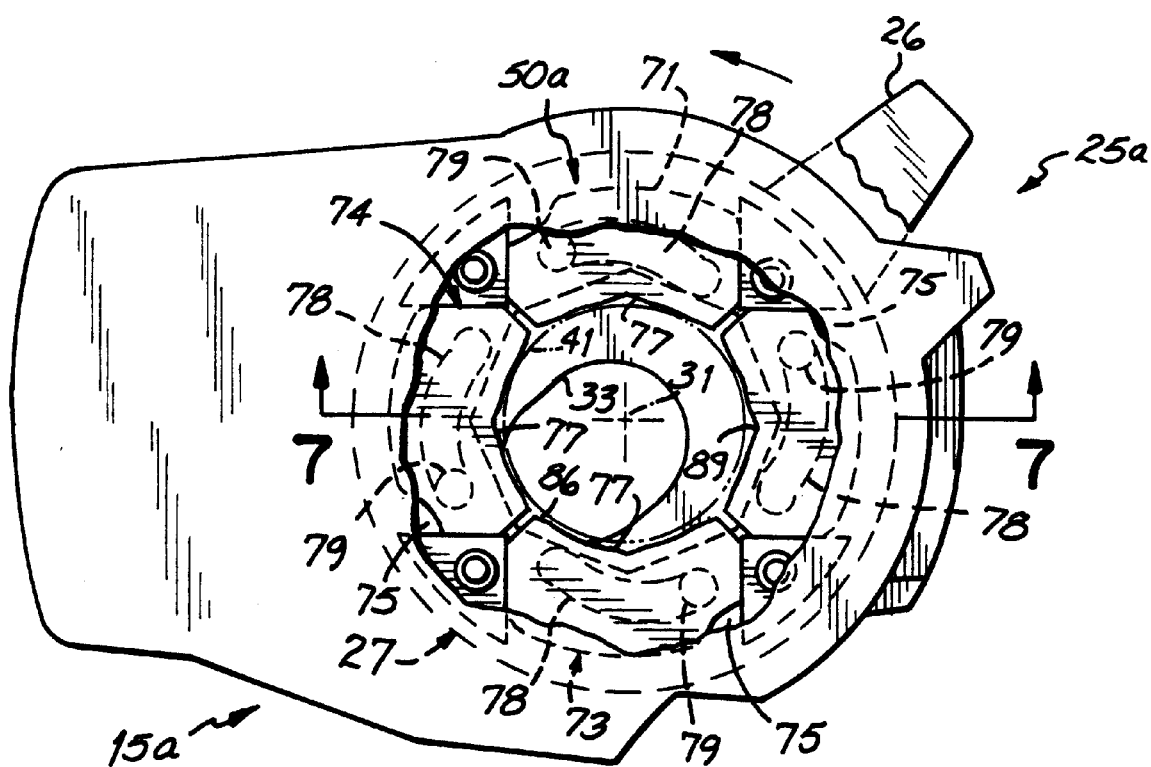
FIG. 6 is a view, similar to FIG. 5, with the gripping structure in a closed or locked position.
Figure 7:
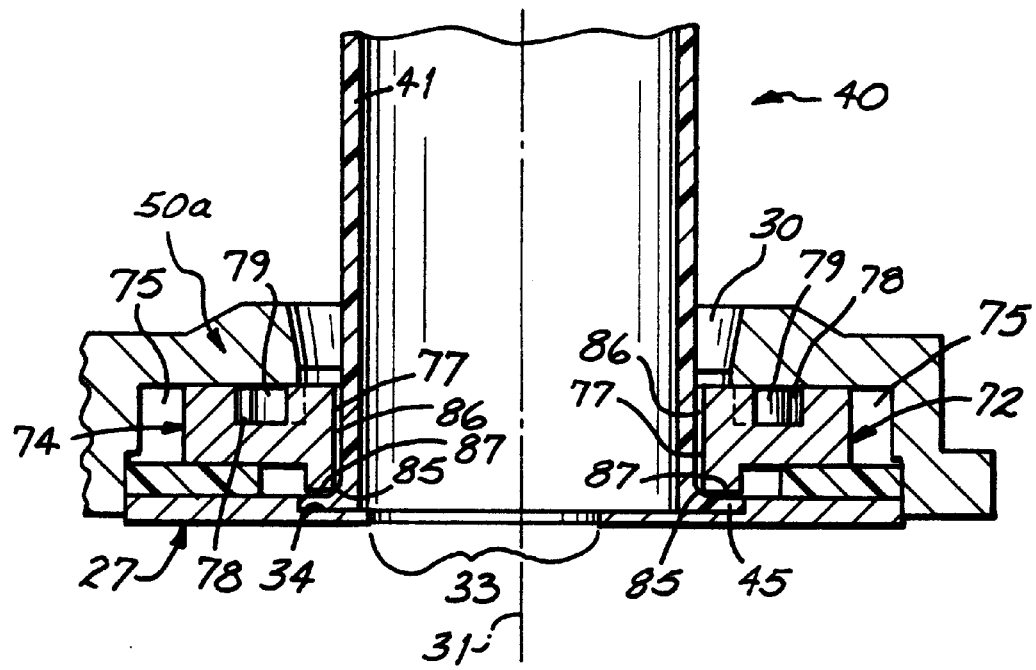
FIG. 7 is a cross-sectional view along line 7—7 of FIG. 6.

According to another embodiment of the invention, an alternative head 15a is provided in which the syringe 40 is held in its operating position by an alternative gripping mechanism 50a having a set of four slidable jaws 71–74, as illustrated in FIGS. 5–7. Each of the jaws 71–74 has a rectangular cross-section when viewed from the axis 31, and each is trapped to slide radially in a respective one of four rectangular slots 75 formed between respective pairs of adjacent ones of a set of four wedges 76, which are fixed to the ring 27, and between the casting 17 and the rotatable ring 27. The jaws 71–74 have inner concave gripping surfaces 77 having curvatures that correspond to the curvature of the outer surface of the body 41 of syringe 40, so that when the jaws 71–74 are closed (FIG. 3) the surfaces 77 substantially surround the body 41 of the syringe 40 and securely hold the syringe in the operating position. The jaws 71–74 are spaced forward of the stop 32 so that, when the syringe 40 is in its operating position, the syringe flange 45 is held flat against the stop 32 by the jaws 71–74.

The jaws 71–74 rotate with the ring 27 and also simultaneously move between retracted positions (FIG. 5) and locked positions (FIG. 6) by the camming action of the mechanism 25a. The gripping surfaces 77 of the jaws 71–75 have V-shaped notches 89 therein which line up with the corners of the recess 34 in the ring 26. Each one of the jaws 71–74 is provided with a cam follower slot 78 in which is located a cam pin 79 which is fixed to the casting 17 and lies on a circle centered on the axis 31. When the handle 26 is operated to move the ring 27, the wedges 76 move with the ring 27 and rotate with them the jaws 71–74. The movement of the jaws 71–74 moves the slots 78 along the fixed pins 79, which causes the jaws 71–74 to move radially when the handle 26 is operated between their retracted positions, in which the gripping surfaces 77 are displaced radially outward of the flange 45 to provide clearance as the flange 45 during loading and unloading of the syringe 40, and their locked positions snugly against the outside of the body 41 of the syringe 40 immediately forward of the flange 45 to hold the syringe 40 in position for operation.

Preferably, as illustrated in FIG. 3, the gripping surfaces, such as surfaces 55,56 of jaws 51,52, span at least approximately 25% of the circumference of the syringe for many syringes. In the embodiment illustrated, the jaws 51,52 have spaces 81,82 between them that each span no more than approximately 10–20% of the circumference. With some syringes, it is preferred that the gripping surfaces span at least approximately 65% of the circumference and in addition or in the alternative, that spaces between contacting portions of the surfaces by not more than approximately 95% of the circumference of the syringe. For example, surfaces 77 of jaws 71–74 in FIG. 6, each have two arcs spaced by a V-shaped notch 89 of less than about 3 to 5% of the circumference, with the spaces 83 between the jaws 71–74, when the jaws are in the locked position, being also spanning less than approximately 3 to 5% of the circumference, leaving about 65% of the circumference cumulatively spanned by the surfaces 77.

While the jaws 51,52 and 71–74 are referred to herein as gripping jaws, these jaws may or may not actually squeeze radially inward on the syringe 40. What is preferred is that they contribute to the holding of the syringe in the opening 30, particularly resisting the force exerted by the ram 12 in moving the plunger 47. It is also important that, whatever holding action is performed by the gripping structure, the syringe 40 be held against the forces of operation without subjecting it to such forces and stresses that would cause any portion of the syringe 40 to fail. To this end, it is preferred that the jaws 51,52 or 71–74 engage the syringe 40 close to the body 41 of the syringe 40, at the intersection of the flange 45 with the syringe body 41, in a way that concentrates axial forces on the syringe 40 on the flange 45 as close to the body 41 as possible. This may be accomplished by configuring the rear edge of the inner surfaces 55,56 or 77 of the jaws 51,52 or 71–74 with a smaller radius than the radius 85 between the flange 45 and the outside of the syringe body 41, as illustrated in FIG. 6. This leaves small spaces 86 between the jaws and the syringe body 41 and spaces 87 between the jaws and the syringe flange 45.

To load a syringe 40 into an injector 10, a faceplate 15 or 15a having a gripping mechanism 50 or 50a is mounted onto the injector housing 11, for example as a replacement to the standard faceplate with which the injector 10 is provided. If the syringe 40 has a plunger coupling that is not compatible with the coupling in the ram 12 of the injector 10, a ram coupling adapter may be attached to the end of the ram 12 to provide coupling between the ram 12 and the coupling element (not shown) on the rear side of the plunger 47.

With the lever 26 in its unlocked position, a syringe 40 is loaded into the opening 30 by translating the syringe 40 in a rearward axial direction, rear end first, until the flange 45 on the rearward end 44 of the syringe 40 passes through the opening 30 and rests in the recess 34 and against the stop plate 32 in the ring 27. The tapered front of the opening 30 in the casting 17 guides the flange 45 such that the shaped perimeter thereof lines up with the similarly shaped periphery of the recess 34. With the lever 26 so unlocked, the jaws 51,52 or 71–74 are in their retracted positions out of the path of the flange 45 as it is inserted into the opening.

When the rearward end 44 of the syringe 40 is completely seated in the opening, the lever 26 is moved to its locked position, which causes the jaws 51,52 or 71–74, to move to their closed positions against the outside of the body 41 of the syringe 40, gripping the body 41 and trapping the flange 45 between the jaws 51,52 or 71–74 and the ring 27. This locking motion securely holds the syringe in position in the holder 15 on the housing 11 of the injector 10, with its plunger 47 in line with the ram 12 and its centerline on the centerline of the holder 31 in alignment with the centerline of the path of the ram 12.

Removal of the syringe is accomplished by moving the lever 26 to its unlocked position to move the jaws 51,52 or 71–74 to their retracted positions. With the injector that is disclosed in U.S. Pat. No. 5,279,569, this movement of the lever causes the locking mechanism 25,25a to slightly rotate the head 15 on the housing 11, which translates the ram 12 out of alignment with the centerline 31 of the opening, thereby shifting the syringe 40 sideways and uncoupling the ram 12 from the syringe plunger 47. The syringe 40 can thereby be manually removed from the injector 10 by translating it forwardly in the axial direction. If there is used injection tubing connected to the nozzle 43 after the use of the syringe 40, the syringe 40 can nonetheless be removed without disconnecting the tubing from the syringe nozzle 43.

Insertion of the syringe 40 into the injector 10 can also be carried out with a simple one handed motion, without separately operating the lever 26. This is accomplished by inserting the syringe in the opening 30 and translating it axially rearwardly until the flange 45 is seated against the stop plate 32 in the recess 34. Then by twisting the syringe 40 in the opening by less than 90°, preferably by about 45°, the ring 26 will turn, operating the locking mechanism 25, which moves the faceplate 15 and syringe plunger 47 into alignment with the ram 12 and operates the gripping mechanism 50,50a to move the jaws 51,52 or 71–74 to their locked position.

The invention provides the user of a power injector with the ability to front load an otherwise rear loadable syringe, particularly a rear loadable syringe having a flange at the rearward end thereof. This provides the user with the advantages of front loadability.

Those skilled in the art will appreciate that the applications of the present invention herein are varied, and that the invention is described in preferred embodiments. Accordingly, additions and modifications can be made to the embodiments of the invention illustrated and described herein without departing from the principles of the invention.

Therefore, what is claimed is:

1. A front-loading injector for supporting a syringe having a fluid cavity containing body, a forward end having a nozzle extending therefrom, and radially outwardly extending support structure on the rearward end of the body and for driving a plunger in the syringe forwardly through the body in a direction parallel to the longitudinal axis of the syringe to inject fluid from a cavity within the body of the syringe and out of the nozzle of the syringe, comprising:

an injector housing having a front with an opening therein and an injection ram in the housing and extendable along an axis of the ram through the opening and beyond the front of the housing to drive a plunger in a syringe mounted to said housing and through the cavity in the body thereof; and locking structure within the opening including elements that are moveable radially to and from an axis through the opening between a retracted position sufficiently spaced from the axis through the opening to permit passage of outwardly extending support structure on the rearward end of the syringe when inserted rearwardly into or removed forwardly from the opening and a locking position in which the elements hold the syringe immediately forward of and against the support structure on the rearward end thereof to thereby lock the syringe to the injector with its longitudinal axis substantially coincident with the axis through the opening with the body of the syringe extending freely beyond and away from the injector, forward of the front of the housing and forward of the moveable elements of the locking structure with the forward end of the body and the nozzle remote from the locking structure.

2. The front-loading injector of claim 1 wherein the elements have syringe engaging surfaces thereon which, when in the locked position, are in contact with the outside of the body of a syringe inserted in the opening.

3. The front-loading injector of claim 1 wherein the elements have syringe engaging surfaces thereon which, when in the locking position, are in contact with a forward facing surface on the support structure at the rearward end of the syringe.

4. The front-loading injector of claim 1 wherein the elements have concave syringe engaging surfaces conforming approximately to the syringe.

5. The front-loading injector of claim 1 wherein:
the elements have syringe engaging surfaces thereon that are moveable when actuated into or out of engagement with the outside of a surface of the syringe; and
the injector includes an actuator, mounted on the housing and linked to the elements, which is operable to actuate the elements into and out of engagement with the syringe.

6. The front-loading injector of claim 1 wherein the locking structure includes a plurality of elements each having a syringe engaging surface, each element being mounted to the injector each about a separate one of a plurality of longitudinal pivot axes angularly spaced around the longitudinal axis of the syringe to pivot the syringe engaging surfaces between their retracted and their locking positions.

7. The front-loading injector of claim 6 wherein the locking structure includes two elements each having a syringe engaging surface which, when the element is in its locking position, extends in an arc more than 90° around the syringe.

8. A front-loading injector for supporting a syringe having radially outwardly extending support structure on the rearward end thereof and for driving a plunger in the syringe forwardly in a direction parallel to the longitudinal axis of the syringe to inject fluid from a cavity within the body of syringe and out of the nozzle of the syringe, comprising:
an injector housing having a front with an opening therein and an injection ram in the housing and extendable along an axis of the ram from the front thereof through the opening to drive a plunger in a syringe mounted to said housing; and
locking structure adjacent the opening including elements that are moveable radially to and from an axis through the opening between a retracted position sufficiently spaced from the axis through the opening to permit passage of outwardly extending support structure on the rearward end of the syringe when inserted rearwardly into or removed forwardly from the opening and a locking position in which the elements hold the syringe immediately forward of the support structure on the rearward end thereof to thereby lock the syringe to the injector with its longitudinal axis substantially coincident with the axis through the opening;
each of the elements having a slot therein; and
an actuator, mounted on the housing and including a plurality of pins, one linked to each of the elements to move in the slot of the element, to actuate the elements into and out of holding engagement with the syringe.

9. The front-loading injector of claim 1 wherein the locking structure includes a plurality of elements each having a syringe engaging surface, each element being mounted to the injector to translate the syringe engaging surfaces of the elements at least partially radially between their retracted and locked positions.

10. The front-loading injector of claim 9 wherein the locking structure includes a plurality of more than two elements each having a syringe engaging surface such that, when the element is in its locking position, the surfaces cumulatively extend in an arc of more than 180° around the syringe.

11. The front-loading injector of claim 1 wherein the elements have syringe engaging surfaces thereon which, when in the locked position, contact a flange of a syringe inserted in the opening primarily at the intersection of the flange with the body of the syringe.

12. The front-loading injector of claim 1 wherein the elements have syringe engaging surfaces thereon cumulatively spanning an angle that includes approximately 25% of the circumference of the body of a syringe inserted in the opening.

13. The front-loading injector of claim 1 wherein the elements have syringe engaging surfaces thereon cumulatively spanning an angle that includes approximately 65% of the circumference of the body of a syringe inserted in the opening.

14. The front-loading injector of claim 1 wherein the elements have syringe engaging surfaces thereon which, when in locking position around a syringe that is held in the opening, have spaces therebetween that are each approximately 5% or less of the circumference of the body of a syringe.

15. A front-loading injector holder for removable attachment to a power injector for enabling the injector for the front loading and removal of a syringe having a fluid cavity containing body, a forward end having a nozzle extending therefrom, and a longitudinal axis and radially outwardly extending support structure on the rearward end thereof, comprising:
a holder housing having a front with an opening therein and a connector to removably support the housing on the front of a power injector; and
locking structure on the housing adjacent the opening and including elements that are moveable radially to and from an axis through the opening between a retracted position sufficiently spaced from the axis to permit passage of outwardly extending support structure on the rearward end of the syringe when inserted rearwardly into or removed forwardly from the opening and a locking position in which the elements hold the syringe forward of the support structure on the rearward end thereof to thereby lock the syringe to the holder with its longitudinal axis coincident with the axis through the opening with the body of the syringe extending forward of the front of the housing and forward of the moveable elements of the locking structure with the forward end of the body and the nozzle remote from the locking structure.

16. The front-loading injector holder of claim 15 wherein elements have syringe engaging surfaces thereon which, when in the locked position, are in contact with the outside of the body of a syringe inserted in the opening.

17. The front-loading injector holder of claim 15 wherein elements have syringe engaging surfaces thereon which, when in the locking position, are in contact with a forward facing surface on the support structure at the rearward end of the syringe.

18. The front-loading injector holder of claim 15 wherein elements have concave syringe engaging surfaces conforming approximately to the curvature of the body of a syringe held in the opening.

19. The front-loading injector holder of claim 15 wherein:
elements have syringe engaging surfaces thereon that are moveable when actuated into or out of engagement with the outside of the surface of the body of a syringe; and
the injector includes an actuator, mounted on the housing and linked to the elements, and operable to actuate the elements into and out of engagement with the syringe.

20. The front-loading injector holder of claim 15 wherein the locking structure includes a plurality of elements each having a syringe engaging surface, each element being mounted to the injector each about a separate one of a plurality of longitudinal pivot axes angularly spaced around the longitudinal axis of the syringe to pivot the syringe engaging surfaces of the elements between their retracted and locking positions.

21. The front-loading injector holder of claim 20 wherein the gripping structure includes a plurality of two elements each having a syringe engaging surface which, when the element is in its locking position, extends in an arc more than 90° around the syringe.

22. A front-loading injector holder for removable attachment to a power injector for enabling the injector for the front loading and removal of a syringe having a longitudinal axis and radially outwardly extending support structure on the rearward end thereof, comprising:
a holder housing having a front with an opening therein and a connector to removably support the housing on the front of a power injector; and
locking structure on the housing adjacent the opening and including elements that are moveable radially to and from an axis through the opening between a retracted position sufficiently spaced from the axis to permit passage of outwardly extending support structure on the rearward end of the syringe when inserted rearwardly into or removed forwardly from the opening and a locking position in which the elements hold the syringe forward of the support structure on the rearward end thereof to thereby lock the syringe to the holder with its longitudinal axis coincident with the axis through the opening;
each of the elements having a slot therein; and
an actuator, mounted on the housing and including a plurality of pins, one linked to each of the elements to move in the respective slot of each element to actuate the elements into and out of engagement with the syringe.

23. The front-loading injector holder of claim 15 wherein the locking structure includes a plurality of elements each having a syringe engaging surface, each element being mounted to the injector to translate the syringe engaging surfaces of the elements at least partially radially between their retracted and locked positions.

24. The front-loading injector holder of claim 23 wherein the locking structure includes a plurality of more than two elements each having a syringe engaging surface, such that, when the element is in its locking position, the surfaces cumulatively extend in an arc of more than 180° around the syringe.

25. The front-loading injector holder of claim 15 wherein the elements have syringe engaging surfaces thereon which, when in the locked position, contact a flange of a syringe inserted in the opening primarily at the intersection of the flange with the body of the syringe.

26. The front-loading injector holder of claim 15 wherein the elements have syringe engaging surfaces thereon cumulatively spanning an angle that includes approximately 25% of the circumference of the body of a syringe inserted in the opening.

27. The front-loading injector holder of claim 15 wherein the elements have syringe engaging surfaces thereon cumulatively spanning an angle that includes approximately 65% of the circumference of the body of a syringe inserted in the opening.

28. The front-loading injector holder of claim 15 wherein the elements have syringe engaging surfaces thereon which, when in locking position around a syringe that is held in the opening, have spaces therebetween that are approximately 5% or less of the circumference of the body of a syringe.

29. A method of front-loading into a power injector a syringe having a forward end, a rearward end, and a longitudinal axis and radially outwardly extending support structure on the rearward end thereof, the method comprising the steps of:
providing a holder having a housing with an opening therein and syringe holding structure thereon within the opening that includes elements moveable in a radial direction toward and away from the center of the opening between an inward locking position and an outward non-locking position, respectively;
positioning the elements in a radially outwardly retracted position away from the center of the opening;
with the elements in the outward retracted non-locking position, manually gripping the syringe rearward of its forward end and translating the syringe axially, rearward end first, into the opening from the front thereof until the outwardly extending support structure on the rearward end of the syringe is rearward of the locking position of the elements; and
then, while still manually gripping the syringe, moving the elements inward from their outward retracted unlocking positions to their respective inward locking positions at which the elements engage the syringe by the support structure and by the rearward end of the body immediately forward of the outwardly extending support structure to thereby hold the syringe fixed in the opening with the radial extending syringe support structure located rearwardly of the elements and the forward end of the syringe extending forwardly of and remote from the elements and injector.

30. A method of front-loading into a power injector a syringe having a longitudinal axis and radially outwardly extending support structure on the rearward end thereof, the method comprising the steps of:
providing a holder having a housing with an opening therein and syringe holding structure thereon adjacent the opening that includes elements moveable in a radial direction toward and away from the center of the opening between an inward locking position and an outward non-locking position, respectively;
positioning the elements in a radially outwardly retracted position away from the center of the opening;
with the elements in the outward retracted non-locking position, translating the syringe axially, rearward end first, into the opening from the front thereof until the outwardly extending support structure on the rearward end of the syringe is rearward of the locking position of the elements; and
then, moving the elements inward from their outward retracted unlocking positions to their respective inward locking positions at which the elements hold the syringe fixed in the opening with the radial extending syringe support structure located rearwardly of the elements;

the step of moving the elements being brought about by a step of manually twisting the syringe in the opening.

31. The method of claim 29 wherein the step of providing the holder includes the step of removably attaching to the injector a faceplate having the holder thereon.

32. A method of adapting a power injector for the front-loading thereon of a syringe of the type having a body with a rearward end having an outwardly extending flange thereon, the method comprising the steps of:

providing a power injector having a ram extendable from a retracted position along a linear path to an extended position;

securing to the front of the injector a faceplate having an opening therein and a plurality of radially moveable jaws spaced behind and around the opening, with the opening surrounding the linear path between the retracted and extended positions of the ram;

the faceplate and jaws being configured such that, when the syringe is inserted rearwardly through the opening until the flange is behind the jaws, the jaws are moveable radially inwardly forward of the flange so as to securely grip the rear end of the syringe with the body projecting forwardly from the faceplate and through the opening.

33. A front-loading injector for the front-loading thereon of a syringe of the type having a body with a rearward end having an outwardly extending flange thereon, the injector comprising:

a housing;

a faceplate on the front of the injector having an opening therein and a plurality of radially moveable jaws spaced behind and around the opening;

a ram moveably mounted inside of the housing and having a forward end extendable from a retracted position inside of the housing behind the faceplate, outwardly through the opening to an extended position forward of the jaws;

the faceplate and jaws being configured such that, when the syringe is inserted rearwardly through the opening until the flange is behind the jaws, the jaws are moveable radially inwardly forward of the flange so as to securely grip the rear end of the syringe with the body projecting forwardly from the faceplate and through the opening.

* * * * *